(12) United States Patent
Ida

(10) Patent No.: US 8,679,017 B2
(45) Date of Patent: Mar. 25, 2014

(54) BIOLOGICAL INFORMATION MEASUREMENT APPARATUS AND METHOD

(75) Inventor: Ichirou Ida, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 450 days.

(21) Appl. No.: 12/507,966

(22) Filed: Jul. 23, 2009

(65) Prior Publication Data

US 2010/0030066 A1 Feb. 4, 2010

(30) Foreign Application Priority Data

Jul. 30, 2008 (JP) .................................. 2008-196794

(51) Int. Cl.
*A61B 8/00* (2006.01)

(52) U.S. Cl.
USPC ........... 600/437; 600/407; 600/485; 600/500; 600/508

(58) Field of Classification Search
USPC .................. 600/407, 437, 480, 481, 485, 500
See application file for complete search history.

(56) References Cited

U.S. PATENT DOCUMENTS

| | | | | |
|---|---|---|---|---|
| 4,714,341 A | * | 12/1987 | Hamaguri et al. ............... | 356/41 |
| 5,535,747 A | | 7/1996 | Katakura | |
| 5,590,662 A | * | 1/1997 | Hersh et al. .................... | 600/494 |
| 5,651,370 A | * | 7/1997 | Hersh et al. .................... | 600/494 |
| 5,833,602 A | * | 11/1998 | Osemwota .................... | 600/310 |
| 6,527,729 B1 | * | 3/2003 | Turcott ........................ | 600/528 |
| 6,987,994 B1 | * | 1/2006 | Mortz .......................... | 600/336 |
| 2002/0137995 A1 | * | 9/2002 | Heckel ......................... | 600/323 |
| 2005/0209517 A1 | * | 9/2005 | Diab et al. .................... | 600/323 |
| 2006/0217612 A1 | * | 9/2006 | Ouchi .......................... | 600/407 |
| 2006/0224074 A1 | * | 10/2006 | Ouchi et al. .................. | 600/513 |
| 2007/0049824 A1 | * | 3/2007 | Konofagou et al. ........... | 600/437 |
| 2007/0083125 A1 | * | 4/2007 | Ouchi et al. .................. | 600/483 |
| 2008/0208021 A1 | * | 8/2008 | Cinbis et al. ................. | 600/324 |
| 2008/0234568 A1 | | 9/2008 | Ouchi | |

FOREIGN PATENT DOCUMENTS

| | | |
|---|---|---|
| JP | 7-241288 | 9/1995 |
| JP | 2001-187032 | 7/2001 |
| JP | 2005-270570 | 10/2005 |

* cited by examiner

*Primary Examiner* — Jonathan Cwern
(74) *Attorney, Agent, or Firm* — Staas & Halsey LLP

(57) ABSTRACT

A biological information measurement apparatus includes an electromagnetic wave applying unit configured to apply, to a living body, a first electromagnetic wave and a second electromagnetic wave having a frequency different from a frequency of the first electromagnetic wave; a reflected wave receiver configured to receive a first reflected wave corresponding to the first electromagnetic wave and a second reflected wave corresponding to the second electromagnetic wave; a correlation value configured to calculate unit calculating a correlation value between the first and second reflected waves; a correlation value evaluating unit configured to determine whether the correlation value satisfies a given condition; and a biological information measuring unit configured to measure biological information based on the first or second reflected wave when the correlation value evaluating unit determines that the correlation value satisfies the given condition.

18 Claims, 8 Drawing Sheets

| CORRELATION VALUE | FREQUENCY#1 | FREQUENCY#2 |
|---|---|---|
| 0.7 | f1 | f2 |
| 0.8 | f2 | f3 |
| 0.6 | f4 | f5 |
| 0.6 | f5 | f6 |
| 0.7 | f6 | f7 |
| ⋮ | ⋮ | ⋮ |

BIOLOGICAL INFORMATION MEASUREMENT APPARATUS AND METHOD

CROSS-REFERENCE TO RELATED APPLICATION

This application is based upon and claims the benefit of priority of prior Japanese Patent Application No. 2008-196794, filed on Jul. 30, 2008, the entire contents of which are incorporated herein by reference.

FIELD

Embodiments of the present invention relate to a biological information measurement apparatus and a biological information measurement method.

BACKGROUND

Information on a living body such as pulsation and blood pressure (hereinafter referred to as "biological information") is measured conventionally by attaching a measurement apparatus such as a sphygmomanometer cuff onto a living body. However, the method of measuring biological information of a subject with a measurement apparatus attached onto a living body sometimes may not accurately measure the biological information because the subject (such as a patient) is aware of the presence of the attached measurement apparatus.

Therefore, a number of contactless biological information measurement apparatuses that measure biological information without needing to be attached to a living body (see for example Japanese Patent Laid-Open No. 2005-270570, No. 2001-187032, and No. 7-241288) have been proposed. For example, a contactless blood-pressure measurement apparatus has been proposed that applies an electromagnetic wave to a living body and detects the electromagnetic wave (reflected wave) scattered from the surface of the living body to measure the blood pressure. Also, a contactless blood-pressure measurement apparatus has been proposed that applies an ultrasound to a living body to measure the blood pressure by determining blood flow using Doppler ultrasound.

However, the biological information measurement apparatuses described above have a problem that the apparatuses may not accurately measure biological information in some situations. In particular, an electromagnetic wave and ultrasound applied to a living body by the biological information measurement apparatuses and the waves reflected by the living body and received by the biological information measurement apparatuses may vary under the influence of the ambient environment such as movement by the subject and obstacles around the subject. Therefore, there is the problem that biological information may not be accurately measured by the biological information measurement apparatuses described above under the influence of the ambient environment.

The technique disclosed herein has been devised in order to address the problem described above and an object of the disclosure is to provide a biological information measurement apparatus and a biological information measurement method capable of accurately measuring biological information.

SUMMARY

According to an aspect of the embodiments discussed herein, a biological information measurement apparatus includes an electromagnetic wave applying unit configured to apply, to a living body, a first electromagnetic wave and a second electromagnetic wave having a frequency different from a frequency of the first electromagnetic wave; a reflected wave receiver configured to receive a first reflected wave corresponding to the first electromagnetic wave and a second reflected wave corresponding to the second electromagnetic wave; a correlation value calculating unit calculating a correlation value between the first and second reflected waves; a correlation value evaluating unit configured to determine whether the correlation value satisfies a given condition; and a biological information measuring unit configured to measure biological information based on the first or second reflected wave when the correlation value evaluating unit determines that the correlation value satisfies the given condition.

It is to be understood that both the foregoing general description and the following detailed description are exemplary and explanatory and are not restrictive of the embodiments, as claimed.

BRIEF DESCRIPTION OF DRAWINGS

FIG. 6 is a diagram illustrating an example of a correlation value storage;

DESCRIPTION OF EMBODIMENTS

Figure 1:
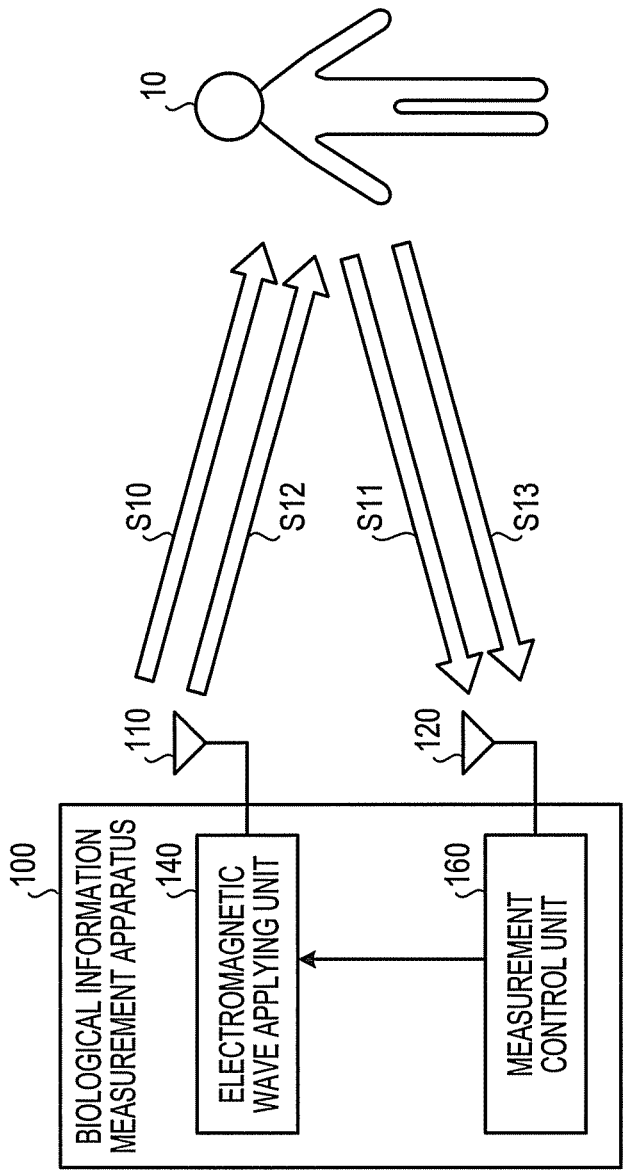
FIG. 1 is a diagram illustrating an overview of a biological information measurement apparatus according to a first embodiment.

Examples of embodiments of a biological information measurement apparatus and a biological information measurement method disclosed herein will be described in detail with reference to the accompanying drawings.

First Embodiment

An overview of a biological information measurement apparatus 100 according to a first embodiment will be described first. The biological information measurement apparatus 100 applies two electromagnetic waves with different frequencies to a living body and receives the electromagnetic waves reflected back from the living body. The biological information measurement apparatus 100 calculates a correlation value between the two reflected waves received and determines whether the calculated correlation value is greater than a given threshold value (hereinafter referred to as the "correlation value threshold"). If the calculated correlation value is greater than the correlation value threshold, the biological information measurement apparatus 100 measures biological information (for example the pulsation) based on the reflected waves.

Here, the reason for calculating the correlation value between the two reflected waves will be described. An electromagnetic wave applied to a living body by the biological information measurement apparatus 100 and the reflected electromagnetic wave with a certain frequency may be affected by the ambient environment. However, whether an electromagnetic wave and reflected waves are being affected by the ambient environment may not be determined by measuring biological information based on only one reflected wave. In medical practice, accurate measurement of biological information such as pulsation is desired because the biological information is used by a doctor as a criterion for diagnosis.

The biological information measurement apparatus 100 makes use of the fact that electromagnetic waves with different frequencies are less likely to be equally affected by an ambient environment. The biological information measurement apparatus 100 applies two electromagnetic waves with different frequencies to a living body and calculates a correlation value between the two reflected waves with the different frequencies. If the correlation value is greater than a correlation value threshold, the waveforms of the two reflected waves are similar to each other and therefore it is likely that the waves are not being affected by the ambient environment. For example, if one of the two frequencies is susceptible to the ambient environment, the correlation value will be small. If both of the frequencies are susceptible to the ambient environment, the possibility of both of the frequencies being exactly equally affected by the ambient environment is low and therefore the correlation value will be small. Therefore, if the correlation value between the two reflected waves is greater than the correlation value threshold, the biological information measurement apparatus 100 determines that electromagnetic waves and reflected waves are not being significantly affected by the ambient environment and then measures the biological information based on the reflected waves.

FIG. 1 is a diagram illustrating an overview of the biological information measurement apparatus 100 according to a first embodiment. An example of the biological information measurement apparatus 100 that measures pulsation as biological information will be described in a first embodiment. As illustrated in FIG. 1, the biological information measurement apparatus 100 includes antennas 110 and 120, an electromagnetic wave applying unit 140, and a measurement control unit 160.

If the pulsation of a subject 10 is to be measured, the electromagnetic wave applying unit 140 of the biological information measurement apparatus 100 applies an electromagnetic wave with a given frequency to the subject 10 through the antenna 110 (step S10). Then, the biological information measurement apparatus 100 receives the applied electromagnetic wave reflected back from the subject 10 through the antenna 120 (step S11).

The electromagnetic wave applying unit 140 then applies an electromagnetic wave with a frequency different from that of the electromagnetic wave applied at step S10 to the subject 10 (step S12) and receives the electromagnetic wave reflected back from the subject 10 (step S13). Then, the measurement control unit 160 of the biological information measurement apparatus 100 calculates a correlation value between the two reflected waves received. If the calculated correlation value is greater than a correlation value threshold, the measurement control unit 160 measures the pulsation based on the reflected waves.

A pulsation measurement method based on reflected waves will be described. Because a living body is oscillating due to its pulsation, air at the surface of the living body is vibrating. Accordingly, when an electromagnetic wave is applied onto the surface of the living body, the electromagnetic wave is analog-modulated by the frequency of the vibration of air. The biological information measurement apparatus 100 receives the analog-modulated reflected wave and extracts the frequency of the vibration of air from the reflected wave to measure the pulsation.

The difference in frequency between the two electromagnetic waves applied by the electromagnetic wave applying unit 140 is preferably large. This is because if the difference in frequency is small, the electromagnetic waves and the reflected waves may be similarly affected by the ambient environment and the correlation value between the reflected waves may be large even though they are affected by the ambient environment.

The biological information measurement apparatus 100 according to the first embodiment applies two electromagnetic waves with different frequencies to a living body and, if a correlation value between the electromagnetic waves reflected back from the living body is larger than a correlation value threshold, measures the pulsation. Therefore, the pulsation may be accurately measured.

Figure 2:
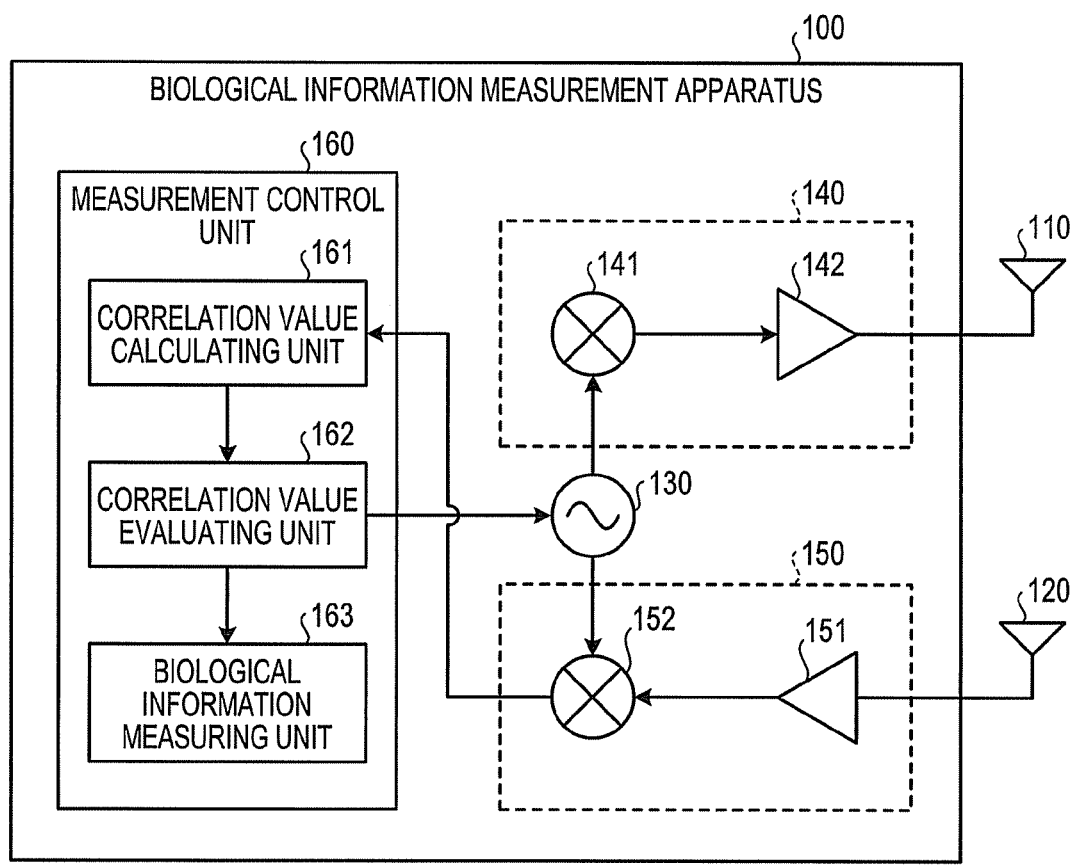
FIG. 2 is a diagram illustrating a configuration of the biological information measurement apparatus according to the first embodiment.

A configuration of the biological information measurement apparatus 100 according to the first embodiment will be described below. FIG. 2 illustrates a configuration of the biological information measurement apparatus 100 according to the first embodiment. As illustrated in FIG. 2, the biological information measurement apparatus 100 includes antennas 110 and 120, a signal generator 130, an electromagnetic wave applying unit 140, a reflected wave receiver 150, and a measurement control unit 160.

The antenna 110 is used for transmitting electromagnetic waves to a living body and the antenna 120 is used for receiving the applied electromagnetic waves reflected back from the living body. The signal generator 130 generates a signal and outputs the signal to mixers 141 and 152, which will be described later.

The electromagnetic wave applying unit 140 is a functional unit that generates electromagnetic waves to be applied to a living body and includes the mixer 141 and an amplifier 142. The mixer 141 uses a signal input from the signal generator 130 to generate an electromagnetic wave having a given frequency and outputs the generated electromagnetic wave to the amplifier 142. The amplifier 142 is a power amplifier (PA) which amplifies an electromagnetic wave input from the mixer 141 and transmits the amplified electromagnetic wave to the outside of the biological information measurement apparatus 100 through the antenna 110.

When the biological information measurement apparatus 100 measures biological information of a subject for the first time, the signal generator 130 outputs two signals with different frequencies to the mixer 141 and the electromagnetic wave applying unit 140 into which the signals are input applies two electromagnetic waves with the different frequencies to a living body. For example, the signal generator 130 outputs a signal with a frequency f1 to the mixer 141 and the electromagnetic wave applying unit 140 applies an electromagnetic wave with the frequency f1 to the living body. Then, the signal generator 130 outputs a signal with a frequency f2 different from the frequency f1 to the mixer 141 and the electromagnetic wave applying unit 140 applies an electromagnetic wave with the frequency f2 to the living body.

The reflected wave receiver 150 is a functional unit that receives an applied electromagnetic wave reflected back from a living body and includes a low noise amplifier 151 and the mixer 152. The low noise amplifier 151 is an amplifying circuit with a low noise factor and amplifies a reflected wave received through the antenna 120 and outputs the amplified reflected wave to the mixer 152. The mixer 152 uses a signal input from the signal generator 130 to convert the frequency of a reflected wave input from the low noise amplifier 151, and outputs the reflected wave with the changed frequency to a correlation value calculating unit 161, which will be described later.

As described above, when the biological information measurement apparatus 100 measures biological information of a subject for the first time, the electromagnetic wave applying unit 140 applies two electromagnetic waves with different frequencies to the living body. The reflected wave receiver 150 sequentially receives the two electromagnetic waves reflected back from the living body. In the example described above, the reflected wave receiver 150 receives the reflected electromagnetic wave with the frequency f1 and the reflected electromagnetic wave with the frequency f2 in this order.

The measurement control unit 160 is a controller that performs measurement of biological information and includes a correlation value calculating unit 161, a correlation value evaluating unit 162, and a biological information measuring unit 163. The correlation value calculating unit 161 is a processing unit that calculates a correlation value between two reflected waves input from the reflected wave receiver 150. In particular, whenever a reflected wave is input from the reflected wave receiver 150, the correlation value calculating unit 161 stores variations in the signal level of the reflected wave with time in a given storage unit (such as a memory). Then, the correlation value calculating unit 161 calculates a correlation value between the two reflected waves stored in the given storage unit.

The correlation value between two reflected waves may be obtained by using the following equation.

$$\text{Correlation value} = \frac{\frac{1}{T_0} \int_{-2/T_0}^{2/T_0} \binom{\text{voltage of reflected}}{\text{wave with frequency } f_n} \binom{\text{voltage of reflected wave}}{\text{with frequency } f_{n-1}} dt}{\sqrt{\binom{\text{electric power of reflected}}{\text{wave with frequency } f_n}\binom{\text{electric power of reflected}}{\text{wave with frequency } f_{n-1}}}} \quad (1)$$

The correlation value evaluating unit 162 is a processing unit that determines whether the correlation value calculated by the correlation value calculating unit 161 satisfies a given condition, for example, whether the correlation value is greater than a correlation value threshold. In particular, the correlation value evaluating unit 162 determines whether the correlation value is greater than a correlation value threshold stored in the given storage unit and, if the correlation value is greater than the correlation value threshold, informs the biological information measuring unit 163 of the fact. On the other hand, if the correlation value is less than or equal to the correlation value threshold, the correlation value evaluating unit 162 directs the signal generator 130 to output a signal with a frequency different from the frequency of any of the previously output signals to the mixer 141. In response to the direction, the signal generator 130 outputs, to the mixer 141, a signal with the frequency different from the frequency of any of the signals previously output.

For example, suppose that the electromagnetic wave applying unit 140 applies an electromagnetic wave with a frequency f1 and an electromagnetic wave with a frequency f2 to a living body, as in the example described above, and the reflected wave receiver 150 receives the reflected wave with the frequency f1 and the reflected wave with the frequency f2. If the correlation value between the reflected waves with the frequencies f1 and f2 is less than or equal to the correlation value threshold, the correlation value evaluating unit 162 directs the signal generator 130 to output a signal with a frequency different from the frequencies f1 and f2 to the mixer 141. In response to the direction, the signal generator 130 outputs a signal with a frequency f3, for example, to the mixer 141 to cause the electromagnetic wave applying unit 140 to apply an electromagnetic wave with the different frequency f3 to the living body. In that case, the reflected wave receiver 150 receives the wave with the frequency f3 reflected back from the living body and the correlation value calculating unit 161 calculates the correlation value between the reflected waves with the frequencies f2 and f3. Then the correlation value evaluating unit 162 determines whether the calculated correlation value is greater than the correlation value threshold. The correlation value evaluating unit 162 continues changing the frequency to be applied to the living body until the correlation value between two reflected waves exceeds the correlation value threshold.

Since the biological information measurement apparatus 100 continues to change the frequency of an electromagnetic wave to be applied to a living body until the correlation value between two reflected waves exceeds the correlation value threshold in this way, the biological information measurement apparatus 100 may accurately measure biological information based on an electromagnetic wave and a reflected wave with a frequency less susceptible to the ambient environment.

The biological information measuring unit 163 is a processing unit that measures biological information from two reflected waves when the correlation value evaluating unit 162 determines that the correlation value is greater than the correlation value threshold. In particular, the biological information measuring unit 163 measures pulsation based on one of the two reflected waves. Similarly, the biological information measuring unit 163 measures pulsation based on the other of the two reflected waves. Then the biological information measuring unit 163 calculates the average value of the two measured pulsation values. Since the biological information measuring unit 163 calculates the average value of two pulsation values in this way, the pulsation may be accurately measured even if one of the reflected waves is affected slightly by the ambient environment.

The biological information measuring unit 163 may measure pulsation based on only one of two reflected waves. This is because the pulsation values measured from the two reflected waves will be approximately equal to each other if the correlation value between the two reflected waves is large. This may reduce the processing load on the biological information measurement apparatus 100.

The biological information measuring unit 163 may display the measured pulsation value on a display unit, store the measured pulsation value in a storage unit, or send the measured pulsation value to another apparatus.

Figure 3:
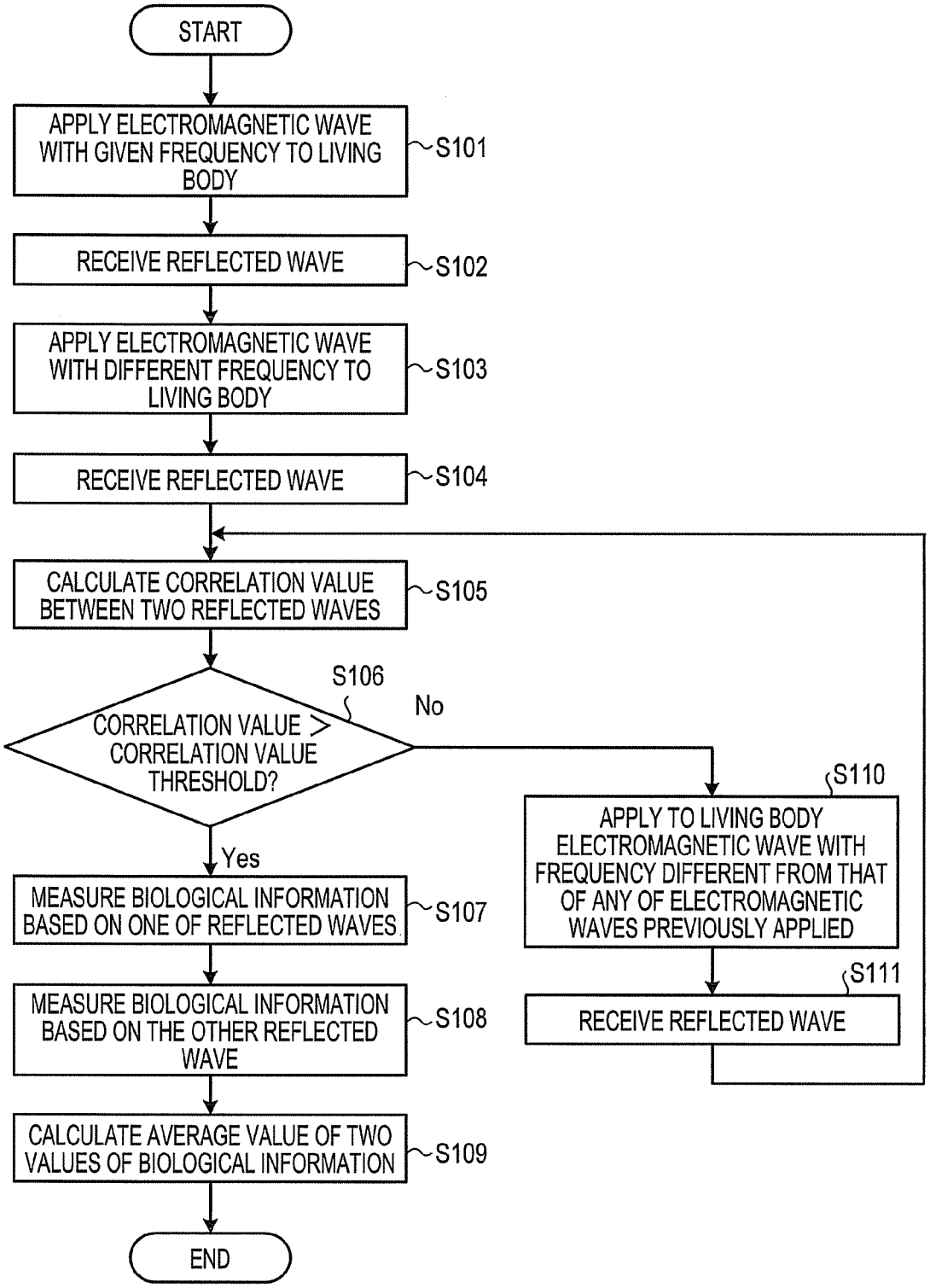
FIG. 3 is a flowchart of a biological information measurement process performed by the biological information measurement apparatus according to the first embodiment.

A biological information measurement process performed by the biological information measurement apparatus 100 will be described below. FIG. 3 is a flowchart of a biological information measurement process by the biological information measurement apparatus 100 according to the first embodiment. As illustrated in FIG. 3, the electromagnetic wave applying unit 140 of the biological information measurement apparatus 100 first applies an electromagnetic wave with a given frequency to a living body (step S101). Then the reflected wave receiver 150 receives the electromagnetic wave reflected back from the living body (step S102), demodulates the received reflected wave, and outputs the demodulated wave to the correlation value calculating unit 161. The correlation value calculating unit 161 stores variations in the signal level of the input reflected wave over time in a storage unit.

Then, the electromagnetic wave applying unit 140 applies an electromagnetic wave with a frequency different from that of the electromagnetic wave applied at step S101 (step S103). The reflected wave receiver 150 receives the electromagnetic wave reflected back from the living body (step S104), demodulates the received reflected wave, and outputs the demodulated reflected wave to the correlation value calculating unit 161. The correlation value calculating unit 161 stores variations in the signal level of the input reflected wave over time in the storage unit.

Then, the correlation value calculating unit 161 calculates the correlation value between the two reflected waves stored in the storage unit (step S105). Here, the correlation value calculating unit 161 calculates the correlation value between the last and second last reflected waves stored among the reflected waves stored in the storage unit.

Then, the correlation value evaluating unit 162 determines whether or not the correlation value calculated by the correlation value calculating unit 161 is greater than a correlation value threshold. If the correlation value evaluating unit 162 determines that the correlation value is greater than the correlation value threshold (YES at step S106), the biological information measuring unit 163 measures biological information based on one of the two reflected waves (step S107) and also measures the biological information based on the other reflected wave (step S108). The biological information measuring unit 163 calculates the average value of the two measured values of biological information (step S109).

On the other hand, if the correlation value evaluating unit 162 determines that the correlation value is less than or equal to the correlation value threshold (NO at step S106), the electromagnetic wave applying unit 140 applies an electromagnetic wave with a frequency different from those of the electromagnetic waves previously applied (step S110). Then the reflected wave receiver 150 receives the electromagnetic wave reflected back from the living body (step S111) and outputs the reflected wave to the correlation value calculating unit 161. The correlation value calculating unit 161 stores variations in the signal level of the input reflected wave over time in the storage unit.

Then the correlation value calculating unit 161 calculates the correlation value between the last and second last reflected wave stored among the reflected waves stored in the storage unit (step S105). That is, the correlation value calculating unit 161 calculates the correlation value between the reflected wave received at step S104 and the reflected wave received at step S111. The correlation value evaluating unit 162 determines whether or not the calculated correlation value is greater than the correlation value threshold.

The biological information measurement apparatus 100 repeats the process sequence of steps S105, S106, S110, and S111 described above until the correlation value between two reflected waves exceeds the correlation value threshold (YES at step S106).

As has been described, the biological information measurement apparatus 100 according to the first embodiment applies two electromagnetic waves with different frequencies to a living body and, if the correlation value between the electromagnetic waves reflected back from the living body is greater than the correlation value threshold, measures biological information based on the reflected waves. Therefore, the biological information measurement apparatus 100 is capable of accurately measuring the biological information.

Since the biological information measurement apparatus 100 continues changing the frequency of an electromagnetic wave to be applied to a living body until the correlation value between two reflected waves exceeds the correlation value threshold, the biological information measurement apparatus 100 may accurately measure biological information based on an electromagnetic wave and reflected electromagnetic wave with a frequency less susceptible to the ambient environment.

Second Embodiment

While an example in which pulsation is measured as biological information has been described in the first embodiment, the biological information measurement apparatus is applicable to measurement of other biological information such as blood pressure as well. An exemplary biological information measurement apparatus that measures blood pressure will be described in a second embodiment.

An overview of a biological information measurement apparatus according to the second embodiment will be described first. The biological information measurement apparatus according to the second embodiment applies two electromagnetic waves with different frequencies to a living body and receives the electromagnetic waves reflected back from the living body while applying ultrasound to the living body. The biological information measurement apparatus calculates a correlation value between the two reflected waves received and determines whether the calculated correlation value is greater than a given correlation value threshold. If the calculated correlation value is greater than the given correlation value threshold, the biological information measurement apparatus measures blood pressure based on the reflected waves.

Figure 4:
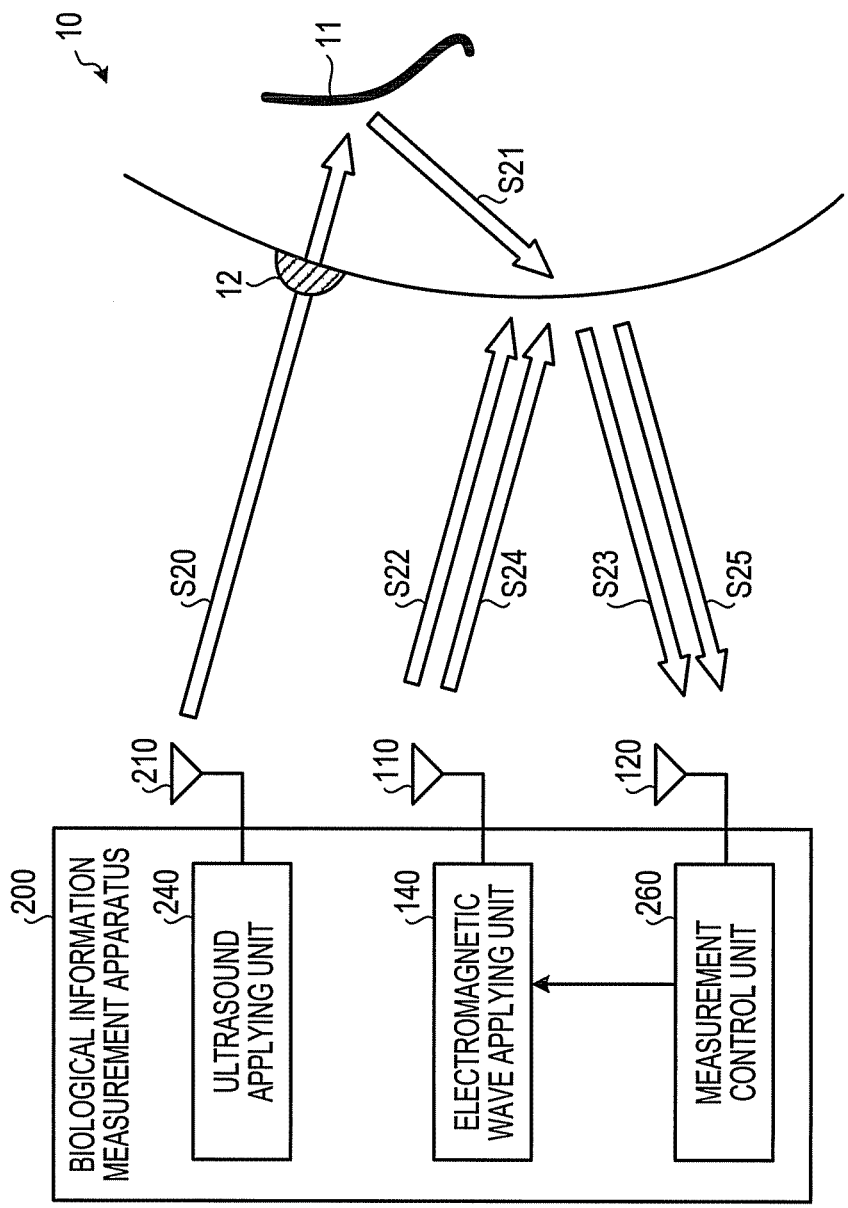
FIG. 4 is a diagram illustrating an overview of a biological information measurement apparatus according to a second embodiment.

FIG. 4 is a diagram illustrating an overview of the biological information measurement apparatus 200 according to the second embodiment. As illustrated in FIG. 4, the biological information measurement apparatus 200 includes antennas 110, 120, and 210, an electromagnetic wave applying unit 140, an ultrasound applying unit 240, and a measurement control unit 260.

When the blood pressure of a subject 10 is to be measured, the ultrasound applying unit 240 of the biological information measurement apparatus 200 applies ultrasound with a given frequency to the subject 10 through the antenna 210 (step S20). The ultrasound is applied to the subject 10 because electromagnetic waves do not reach a blood vessel 11 inside an organ of the subject 10 whereas ultrasound reaches the blood vessel 11 in the organ. It is desirable that a matching layer 12 of an appropriate material be applied to the surface of the body of the subject 10 in order to facilitate transmission of the ultrasound into the organ.

The ultrasound transmitted to the blood vessel 11 is reflected back (step S21). At this time point, a Doppler effect is caused by the velocity of blood flow in the blood vessel 11, which causes a difference between the frequency of the ultrasound transmitted to the blood vessel 11 and the frequency of the reflected ultrasound. The difference in frequency causes a beat and air at the surface of the living body vibrates at the frequency of the beat.

Then the electromagnetic wave applying unit 140 applies an electromagnetic wave with a given frequency to the subject 10 (step S22) and receives the electromagnetic wave reflected back from the subject 10 through the antenna 120 (step S23). The electromagnetic wave applying unit 140 then applies an electromagnetic wave with a frequency different from that of the electromagnetic wave applied at step S22 (step S24) and receives the electromagnetic wave reflected back from the subject 10 (step S25).

Then the measurement control unit 260 of the biological information measurement apparatus 200 calculates the correlation value between the two received reflected waves. If the calculated correlation value is greater than the correlation value threshold, the measurement control unit 260 measures the blood pressure based on the reflected waves. A method for measuring the blood pressure from the reflected waves will be described later.

In this way, the biological information measurement apparatus 200 according to the second embodiment applies two electromagnetic waves with different frequencies to a living body while applying ultrasound to the living body and, if the correlation value between the electromagnetic waves reflected back from the living body is greater than the correlation value threshold, measures the blood pressure. Therefore the biological information measurement apparatus 200 may accurately measure the blood pressure.

Figure 5:
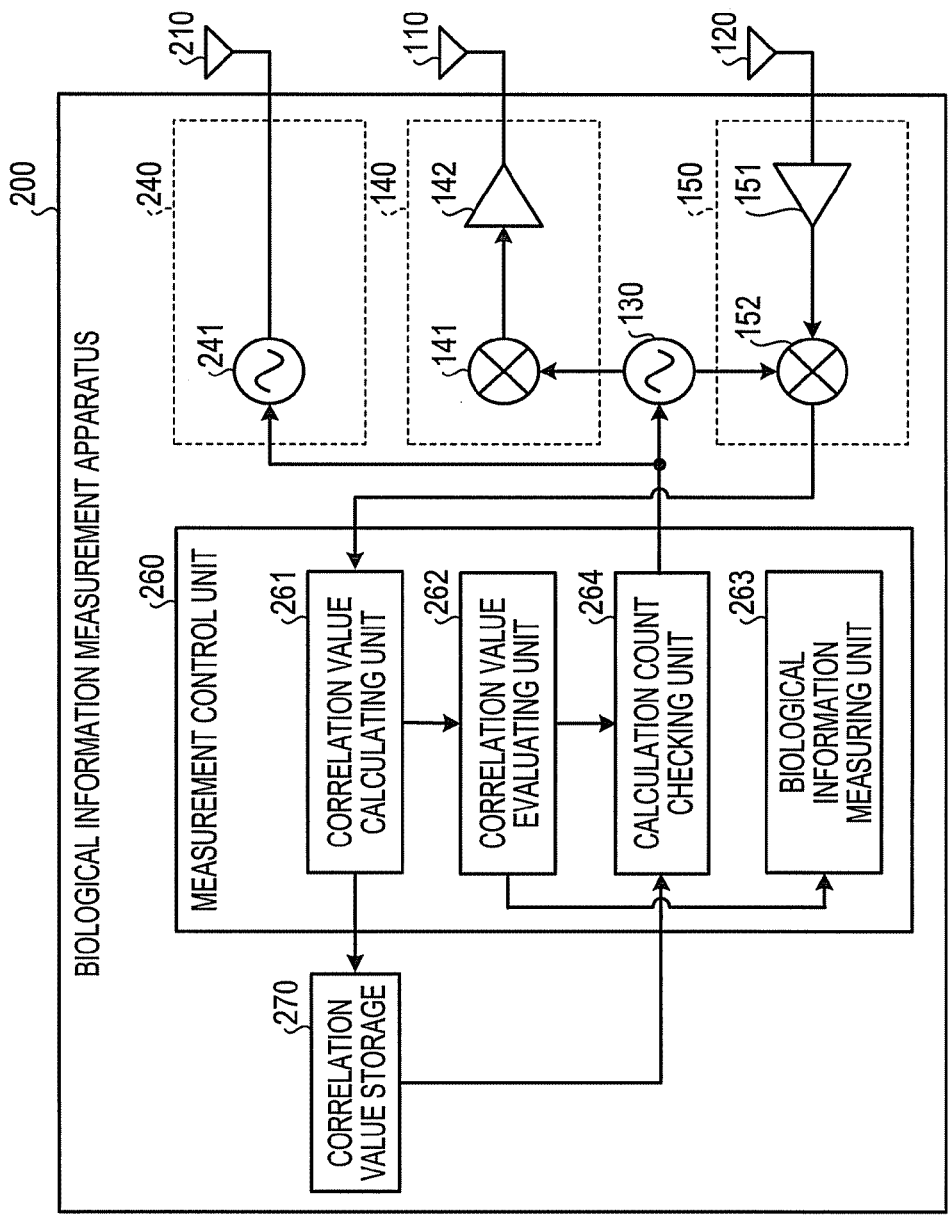
FIG. 5 is a diagram illustrating a configuration of the biological information measurement apparatus according to the second embodiment.

A configuration of the biological information measurement apparatus 200 according to the second embodiment will be described next. FIG. 5 illustrates a configuration of the biological information measurement apparatus 200 according to the second embodiment. As illustrated in FIG. 5, the biological information measurement apparatus 200 includes an antenna 210, an ultrasound applying unit 240, and a correlation value storage 270 in addition to the components of the biological information measurement apparatus 100 illustrated in FIG. 2. The biological information measurement apparatus 200 includes a measurement control unit 260 in place of the measurement control unit 160 of the biological information measurement apparatus 100 illustrated in FIG. 2.

The antenna 210 is used for transmitting ultrasound to a living body. The ultrasound applying unit 240 is a functional unit that generates ultrasound to be applied to a living body and includes an ultrasound generator 241. The ultrasound generator 241 generates ultrasound and transmits the ultrasound to the outside of the biological information measurement apparatus 200 through the antenna 210.

The correlation value storage unit 270 is a storage unit updated by a correlation value calculating unit 261, which will be described later, and stores a correlation value in association with the frequencies of electromagnetic waves applied to a subject 10 to calculate the correlation value. FIG. 6 illustrates an example of the correlation value storage unit 270. As illustrated in FIG. 6, the correlation value storage unit 270 includes columns such as "Correlation value", "Frequency #1", and "Frequency #2".

For example, the first row of the correlation value storage 270 illustrated in FIG. 6 indicates that the correlation value between a reflected electromagnetic wave with a frequency f1 and a reflected electromagnetic wave with a frequency f2 is 0.7. The second row of the correlation value storage 270 illustrated in FIG. 6 indicates that the correlation value between the reflected electromagnetic wave with the frequency f2 and a reflected electromagnetic wave with a frequency f3 is 0.8.

The measurement control unit 260 includes a correlation value calculating unit 261, a correlation value evaluating unit 262, a calculation count checking unit 264, and a biological information measuring unit 263. The correlation value calculating unit 261 is a processing unit that calculates the correlation value between two reflected waves input from the reflected wave receiver 150. The correlation value calculating unit 261 stores the calculated correlation value and the frequencies of the electromagnetic waves applied to the subject 10 to calculate the correlation value in the correlation value storage unit 270.

For example, suppose that the correlation value calculating unit 261 has calculated a correlation value of 0.6 between reflected electromagnetic wave with a frequency f5 and a reflected electromagnetic wave with a frequency f6. In that case, the correlation value calculating unit 261 stores "f5" in the Frequency #1 column and "f6" in the Frequency #2" column in association with the correlation value "0.6" as illustrated in the fourth row of the correlation value storage unit 270 illustrated in FIG. 6.

The correlation value evaluating unit 262 is a processing unit that determines whether the correlation value calculated by the correlation value calculating unit 261 is greater than a correlation value threshold. In particular, if the correlation value is greater than the correlation value threshold, the correlation value evaluating unit 262 informs the biological information measuring unit 263 of the fact. On the other hand, if the correlation value is less than or equal to the correlation value threshold, the correlation value evaluating unit 262 informs the calculation count checking unit 264 of the fact.

The calculation count checking unit 264 is a processing unit that counts correlation value calculations performed by the correlation value calculating unit 261 (hereinafter referred to as the "calculation count") and determines whether the calculation count is greater than a given threshold value (hereinafter referred to as the "calculation count threshold"). In particular, if the correlation value evaluating unit 262 determines that the correlation value is less than or equal to the correlation value threshold, the calculation count checking unit 264 determines whether or not the calculation count is greater than the calculation count threshold.

If the calculation count is greater than the calculation count threshold, the calculation count checking unit 264 directs the ultrasound generator 241 to apply, to the living body, ultrasound with a frequency different from that of ultrasound previously applied to the living body. In response to the direction, the ultrasound generator 241 applies, to the living body, ultrasound with a frequency different from that of ultrasound previously applied to the living body.

The calculation count checking unit 264 obtains a combination of frequencies #1 and #2 stored in association with the largest correlation value from the correlation value storage unit 270. The calculation count checking unit 264 directs the signal generator 130 to output signals with the two frequencies obtained. In response to the direction, the signal generator 130 outputs the signals with the two frequencies indicated by the calculation count checking unit 264 to the mixer 141 in sequence. The electromagnetic wave applying unit 140 applies electromagnetic waves with the frequencies input from the mixer 141 to the living body.

On the other hand, if the calculation count is less than or equal to the calculation count threshold, the calculation count checking unit 264 directs the signal generator 130 to output a signal with a frequency different from those of the previously output signals to the mixer 141. In response to the direction, the signal generator 130 outputs a signal with a frequency different from those of the previously output signals to the mixer 141. Then the electromagnetic wave applying unit 140 applies an electromagnetic wave with the frequency input from the mixer 141 to the living body.

For example, assume the calculation count is "1" (initial value), the calculation count threshold is "5", and the electromagnetic wave applying unit 140 has applied electromagnetic waves with frequencies f1 and f2 to the living body. In that case, the correlation value calculating unit 261 calculates the correlation value between the reflected electromagnetic waves with the frequencies f1 and f2 and stores information in the correlation value storage unit 270 as illustrated in the first row in the correlation value storage unit 270 in FIG. 6.

It is assumed here that the correlation value evaluating unit 262 determines that the correlation value is less than or equal to the correlation value threshold. In this case, the calculation count is "2". Since the calculation count is less than the calculation count threshold "5", the calculation count checking unit 264 directs the signal generator 130 to output a signal with a frequency different from the frequencies f1 and f2 to the mixer 141. In response to the direction, the signal generator 130 outputs a signal with a frequency f3, for example, to the mixer 141 and the electromagnetic wave applying unit 140 applies an electromagnetic wave with the frequency f3 to the living body.

Then the correlation value calculating unit 261 calculates the correlation value between the reflected waves with the frequencies f2 and f3 and stores information in the correlation value storage unit 270 as illustrated in the second row of the correlation value storage 270 illustrated in FIG. 6. It is assumed here that the correlation value evaluating unit 262 then determines that the correlation value is less than or equal to the correlation value threshold. Here, the calculation count is "3". Since the calculation count is less than the calculation count threshold "5", the calculation count checking unit 264 directs the signal generator 130 to output signals with the frequencies f1, f2, and f3 to the mixer 141. The electromagnetic wave applying unit 140 applies an electromagnetic wave with a frequency f4, for example, to the living body.

It is assumed here that the process described above has been repeated until the calculation count reaches "5" and the information illustrated in FIG. 6 is stored in the correlation value storage 270. Then, assume the correlation value evaluating unit 262 determines that the correlation value between reflected waves with frequencies f6 and f7 is less than or equal to the correlation value threshold. In this case, the calculation count reaches "6". Since the calculation count is greater than the calculation count threshold "5", the calculation count checking unit 264 directs the ultrasound generator 241 to apply to the living body ultrasound with a frequency different from those of the ultrasounds previously applied to the living body. In response to the direction, the ultrasound generator 241 applies to the living body ultrasound with a frequency different from those of the ultrasounds previously applied to the living body.

The calculation count checking unit 264 obtains from the correlation value storage unit 270 a combination of the frequencies #1 and #2 stored in association with the largest correlation value stored. When the correlation value storage unit 270 contains the information illustrated in FIG. 6 in the example described above, the calculation count checking unit 264 obtains the frequencies #1 "f2" and #2 "f3" associated with the correlation value "0.8" from the correlation value storage unit 270. The calculation count checking unit 264 then directs the signal generator 130 to output signals with the frequencies f1 and f2 obtained. Consequently, the electromagnetic wave applying unit 140 applies electromagnetic waves with the frequencies f2 and f3 in sequence to the living body.

The biological information measuring unit 263 is a processing unit that measures blood pressure from two reflected waves if the correlation value evaluating unit 262 determines that the correlation value is greater than the correlation value threshold. In particular, the biological information measuring unit 263 measures blood pressure based on one of the two reflected waves and then measures blood pressure based on the other reflected wave. The biological information measuring unit 263 then calculates the average value of the two measured blood pressures.

A blood pressure measurement method by the biological information measuring unit 263 will be described more specifically below. As stated above, application of ultrasound to a living body causes air at the surface of the living body to vibrate at the frequency of a beat. An electromagnetic wave applied while the air is vibrating is reflected back as a wave analog-modulated with the frequency of the beat. The biological information measuring unit 263 demodulates the reflected wave to extract the frequency of the beat. Since the frequency of the beat is proportional to the velocity of the blood flow, the biological information measuring unit 263 may obtain the dynamic pressure of the blood flow according to the following equation.

$$(\text{dynamic pressure of fluid}) = \tfrac{1}{2} \times (\text{fluid density}) \times (\text{flow velocity of fluid})^2 \quad (2)$$

Here, the "fluid (blood) density" in Equation (2) is an unknown quantity but is an approximately constant value consistent from person to person. Accordingly, a fixed value is assigned to the term "fluid (blood) density" in Equation (2). The biological information measurement apparatus 200 may store the blood density of each subject beforehand and change the value to assign to the "fluid (blood) density" in Equation (2) according to the subject under measurement.

The biological information measuring unit 263 may use the dynamic pressure of blood flow obtained according to Equation (2) to obtain the blood pressure according to the following equation.

$$(\text{blood pressure}) = (\text{lateral pressure of blood flow}) + (\text{dynamic pressure of blood flow}) \quad (3)$$

Here, the "lateral pressure of blood flow" in Equation (3) is an unknown quantity. However, the biological information measuring unit 263 may obtain the blood pressure from only the dynamic pressure of blood flow if the lateral pressure of blood flow of the subject is significantly smaller than the dynamic pressure of the blood flow. The biological information measurement apparatus 200 may store the ratio between the lateral pressure and the dynamic pressure of blood flow of each subject beforehand and may multiply the dynamic pressure of blood flow of each subject by the ratio to obtain the lateral pressure of blood flow of the subject. In this way, the biological information measuring unit 263 measures blood pressure.

The reason why determination is made as to whether the correlation value between two reflected waves is greater than a correlation value threshold in order to accurately obtain waveforms of reflected waves will be described below. If the direction of blood flow is the direction in which the blood flows away from the biological information measurement apparatus 200, the following equation holds between the frequency fs of ultrasound before being affected by the Doppler effect due to blood flow and the frequency fs' of the reflected wave affected by the Doppler effect.

$$fs' = fs - fd \quad (4)$$

Here, "fd" in Equation (4) is the beat component. Then, "fs", "fd" and the apparent flow velocity "v" of blood may be represented as follows.

$$fd = (2 \cdot fs \cdot v)/c \quad (5)$$

Here, "c" in Equation (5) is the speed of sound in the living body (approximately 1530 m/s). The apparent flow velocity "v" of blood may be represented as follows.

$$v = V \cdot \cos \theta \quad (6)$$

where θ is the angle between the irradiation direction of ultrasound and the direction of the blood flow (the direction of the blood vessel).

From Equations (5) and (6), the relation between the apparent flow velocity "v" of blood and the true flow velocity "V" of blood may be represented as follows.

$$V = (fd/fs) \cdot (c/(2 \cos \theta)) \quad (7)$$

As illustrated in Equation (7), the beat component "fd" directly affects the velocity of blood flow. That is, if there is an error in the measurement of "fd", the velocity of blood flow may not accurately be measured. Especially, the dynamic pressure of blood flow is affected by the square of an error because the dynamic pressure of blood flow is calculated by using the square of the blood flow velocity. Therefore, the biological information measurement apparatus 200 according to the second embodiment determines whether the correlation value between two reflected waves is greater than the correlation value threshold to accurately obtain the waveforms of the reflected waves, thereby measuring biological information accurately.

Figure 7:
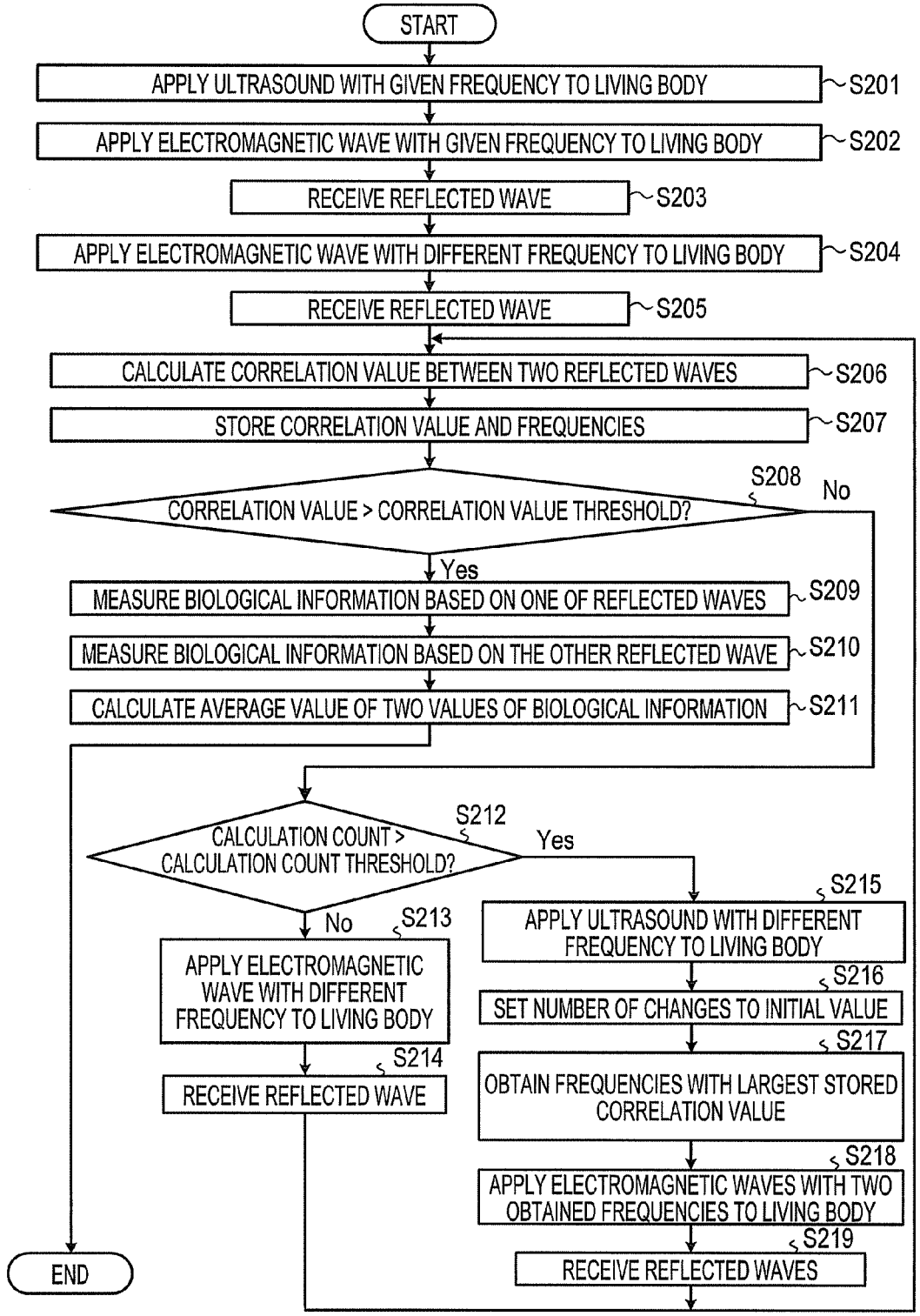
FIG. 7 is a flowchart of a biological information measurement process performed by the biological information measurement apparatus according to the second embodiment.

A biological information measurement process performed by the biological information measurement apparatus 200 will be described next. FIG. 7 is a flowchart of a biological information measurement process by the biological information measurement apparatus 200 according to the second embodiment. As illustrated in FIG. 7, first the ultrasound applying unit 240 of the biological information measurement apparatus 200 applies ultrasound with a given frequency to a living body (step S201).

Then, the electromagnetic wave applying unit 140 applies an electromagnetic wave with a given frequency to the living body (step S202). The reflected wave receiver 150 receives the electromagnetic wave reflected back from the living body (step S203), demodulates the received reflected wave, and then outputs the demodulated reflected wave to the correlation value calculating unit 261. Here, the correlation value calculating unit 261 stores variations in the signal level of the input reflected wave over time in a given storage unit.

Then the electromagnetic wave applying unit 140 applies an electromagnetic wave with a frequency different from the frequency of the electromagnetic wave applied at step S202 to the living body (step S204). The reflected wave receiver 150 receives the electromagnetic wave reflected back from the living body (step S205), demodulates the received reflected wave, and then outputs the demodulated reflected wave to the correlation value calculating unit 261. Here, the correlation value calculating unit 261 stores variations in the signal level of the input reflected wave over time in the given storage unit.

The correlation value calculating unit 261 calculates the correlation value between the last and second last reflected wave stored among the reflected waves stored in the given storage unit (step S206). The correlation value calculating unit 261 stores the calculated correlation value and the frequencies of the electromagnetic waves applied to the subject 10 to calculate the correlation value in the correlation value storage unit 270 (step S207).

The correlation value evaluating unit 262 determines whether the correlation value calculated by the correlation value calculating unit 261 is greater than a correlation value threshold. If the correlation value evaluating unit 262 determines that the correlation value calculated is greater than the correlation value threshold (YES at step S208), the biological information measuring unit 263 measures the biological information based on one of the two reflected waves (step S209) and also measures the biological information based on the other reflected wave (step S210). The biological information measuring unit 263 calculates the average value of the two measured values of biological information (step S211).

On the other hand, if the correlation value evaluating unit 262 determines that the correlation value is less than or equal to the correlation value threshold (NO at step S208), the calculation count checking unit 264 determines whether or not the calculation count is greater than a calculation count threshold. If the calculation count checking unit 264 determines that the calculation count is less than or equal to the calculation count threshold (NO at step S212), the electromagnetic wave applying unit 140 applies, to the living body, an electromagnetic wave with a frequency different from those of electromagnetic waves previously applied (step S213).

Then, the reflected wave receiver 150 receives the electromagnetic wave reflected back from the living body (step S214), demodulates the received reflected wave, and outputs the demodulated reflected wave to the correlation value calculating unit 261. The correlation value calculating unit 261 stores variations in the signal level of the reflected wave received from the reflected wave receiver 150 over time in the given storage unit. The correlation value calculating unit 261 then calculates the correlation value between the last and second last reflected waves stored among the reflected waves stored in the given storage unit (step S206). The correlation value calculating unit 261 stores the calculated correlation value and the frequencies of the electromagnetic waves applied to the subject 10 to calculate the correlation value in the correlation value storage unit 270 (step S207). The correlation value evaluating unit 262 determines whether the calculated correlation value is greater than the correlation value threshold.

On the other hand, if the calculation count checking unit 264 determines that the calculation count is greater than the calculation count threshold (YES at step S212), the ultrasound applying unit 240 applies ultrasound with a frequency different from that of ultrasound previously applied to the living body (step S215). Then the calculation count checking unit 264 updates the calculation count internally managed to the initial value (step S216) and obtains a combination of the frequencies #1 and #2 stored in association with the largest correlation value from the correlation value storage unit 270 (step S217). The electromagnetic wave applying unit 140 applies an electromagnetic wave with the frequency obtained by the calculation count checking unit 264 (step S218).

Then the reflected wave receiver 150 receives the electromagnetic waves applied to the living body at step S218 and reflected back from the living body (step S219), demodulates the received reflected wave, and outputs the demodulated wave to the correlation value calculating unit 261. In particular, after receiving the first electromagnetic wave applied by the electromagnetic wave applying unit 140 and reflected back from the living body, the reflected wave receiver 150 receives the second electromagnetic wave applied by the electromagnetic wave applying unit 140 and reflected back.

The biological information measurement apparatus 200 repeats the sequence of steps S206 through S208 and S212 through S219 until the correlation value between two reflected waves exceeds the correlation value threshold (YES at step S208).

As has been described above, the biological information measurement apparatus 200 according to the second embodiment applies two electromagnetic waves with different frequencies to a living body while applying ultrasound to the living body and, if the correlation value between the electromagnetic waves reflected back from the living body is greater than the correlation value threshold, measures biological information based on the reflected waves. Therefore, the biological information measurement apparatus 200 may accurately measure blood pressure.

Since the biological information measurement apparatus 200 according to the second embodiment changes the frequency of ultrasound to be applied to a living body when the calculation count exceeds the calculation count threshold, the biological information measurement apparatus 200 may apply ultrasound with a frequency insusceptible to ambient environment even if the ultrasound applied to the living body has been affected by the ambient environment.

When the biological information measurement apparatus 200 according to the second embodiment has changed the frequency of ultrasound to be applied to a living body, the biological information measurement apparatus 200 applies electromagnetic waves with frequencies at which the largest correlation value has been obtained before the change of the frequency to the living body. Therefore, the frequencies of the electromagnetic waves at which the correlation value exceeds the correlation value threshold may be efficiently used.

Figure 8:
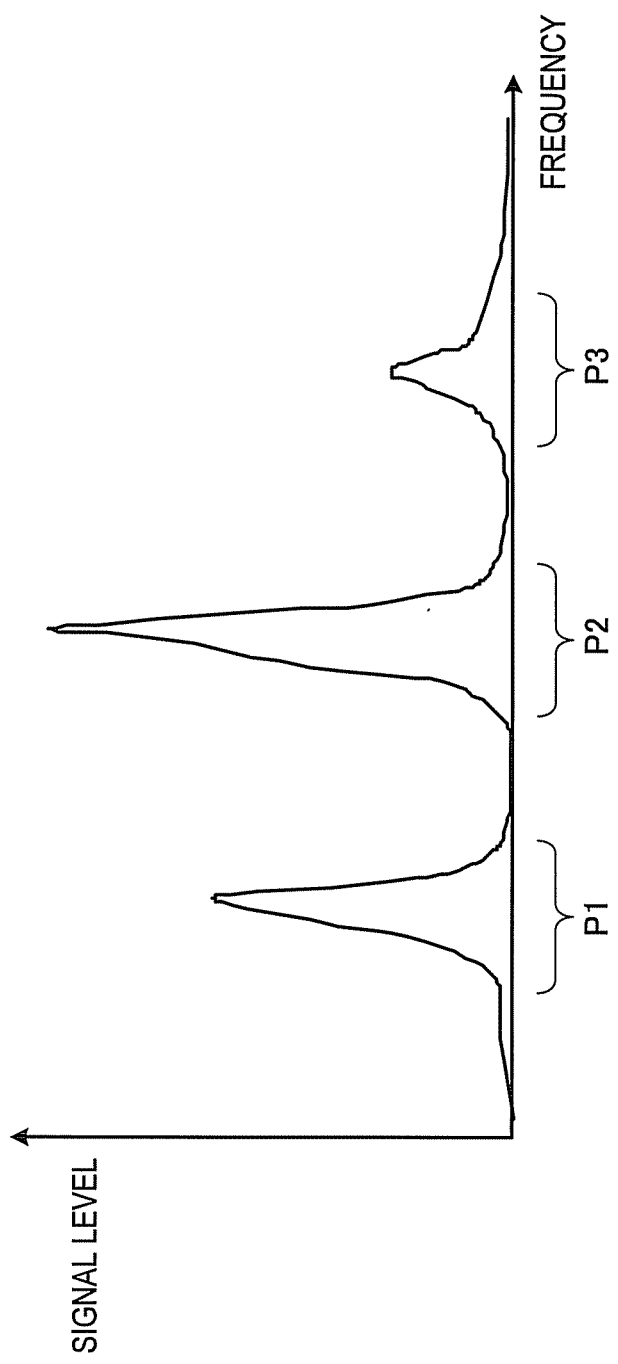
FIG. 8 is a diagram illustrating an example of a reflected wave.

The biological information measuring units 163 and 263 in the first and second embodiments may apply a Fast-Fourier-Transform (FFT) to reflected waves to filter out signal components unnecessary for measuring biological information and then measure the biological information. Referring to FIG. 8, the method will be described in detail. FIG. 8 illustrates an example of a reflected wave. Portion P3 of the signal illustrated in FIG. 8 is required for measuring biological information. The reflected wave includes a signal portion that appears due to the Doppler effect of the running velocity when a subject is running such as portion P1 of the signal in FIG. 8, and a signal portion that appears due to the Doppler effect of movement of the body (a limb) of the subject such as portion P2 in FIG. 8. Therefore, the biological information measuring units 163 and 263 apply a FFT to the reflected wave to extract only the signal portion P3 required for measuring biological information and then measure the biological information. The biological information measurement apparatus may be effectively applied to the measurement of the biological information of a subject running in a gym or outdoors, for example.

While the first and second embodiments have been described with respect to examples in which pulsation or blood pressure is measured as the biological information, the biological information measurement apparatuses of the first and second embodiment are capable of measuring other biological information such as a heartbeat. The biological information measurement apparatuses are capable of measuring biological information of an animal other than humans as well.

While the first and second embodiments have been described with respect to examples in which determination is made as to whether the correlation value between two reflected waves is greater than a correlation value threshold, a correlation value among more than two reflected waves may be calculated and determination may be made as to whether the correlation value is greater than a correlation value threshold.

As has been described, the biological information measurement apparatus according to any of the first and second embodiments is capable of accurately measuring biological information.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A biological information measurement apparatus comprising:
   an ultrasound applying unit configured to apply ultrasound to a living body;
   an electromagnetic wave applying unit configured to apply, to a living body, a first electromagnetic wave and a second electromagnetic wave having a frequency different from a frequency of the first electromagnetic wave, while the ultrasound is being applied to the living body;
   a reflected wave receiver configured to receive a first reflected wave corresponding to the first electromagnetic wave and a second reflected wave corresponding to the second electromagnetic wave;
   a correlation value calculating unit configured to calculate a correlation value between the first and second reflected waves;
   a correlation value evaluating unit configured to determine whether the correlation value satisfies a given condition;
   a biological information measuring unit configured to measure biological information based on at least one of the first and second reflected waves when the correlation value evaluating unit determines that the correlation value satisfies the given condition; and
   a calculation count checking unit configured to count correlation value calculations performed by the correlation value calculating unit and determine whether a calculation count is greater than a given calculation count threshold,
   wherein the electromagnetic wave applying unit continuously changes a frequency applied to a subject by applying an output signal having a different frequency from a signal previously applied until the correlation value between the first and second reflected waves exceeds a correlation value threshold,
   the correlation value calculating unit calculates the correlation value and stores, in a correlation value storage unit, the calculated correlation value and frequencies of the two electromagnetic waves corresponding to the calculated correlation value,
   the ultrasound applying unit changes a frequency of ultrasound to be applied to the living body when the calculation count checking unit determines that the calculation count is greater than the calculation count threshold, and
   wherein the electromagnetic wave applying unit obtains frequencies corresponding to the highest correlation value from the correlation value storage unit and applies two electromagnetic waves having the obtained frequencies to the living body when the calculation count checking unit determines that the calculation count is greater than the calculation count threshold.

2. The biological information measurement apparatus according to claim 1, wherein
the correlation value evaluating unit determines whether the correlation value is greater than the correlation value threshold, and
the biological information measuring unit measures the biological information when the correlation value evaluating unit determines that the correlation value is greater than the correlation value threshold.

3. The biological information measurement apparatus according to claim 1, wherein
when the correlation value evaluating unit determines that the correlation value does not satisfy the given condition, the electromagnetic wave applying unit applies a third electromagnetic wave having a frequency different from frequencies of the first and second electromagnetic waves to the living body,
the reflected wave receiver receives a third reflected wave corresponding to the third electromagnetic wave,
the correlation value calculating unit calculates another correlation value between the second and third reflected waves,
the correlation value evaluating unit determines whether the other correlation value satisfies the given condition, and
when the correlation value evaluating unit determines that the other correlation value satisfies the given condition, the biological information measuring unit measures the biological information based on at least one of the second and third reflected wave.

4. The biological information measurement apparatus according to claim 3, wherein
when the correlation value evaluating unit determines that the correlation value is less than or equal to the correlation value threshold, the electromagnetic wave applying unit applies the third electromagnetic wave to the living body,
the correlation value evaluating unit determines whether the other correlation value is greater than the correlation value threshold and
when the correlation value evaluating unit determines that the other correlation value is greater than the correlation value threshold, the biological information measuring unit measures the biological information.

5. The biological information measurement apparatus according to claim 1, wherein
the biological information measuring unit measures, as the biological information, an average value of the biological information measured based on each of the two reflected waves used to calculate the correlation value.

6. The biological information measurement apparatus according to claim 1, wherein
the biological information measuring unit measures, as the biological information, a pulsation of a living body.

7. The biological information measurement apparatus according to claim 1, wherein
the biological information measuring unit measures a blood pressure of the living body as the biological information.

8. The biological information measurement apparatus according to claim 1, wherein the biological information measuring unit determines that the first and second reflected waves are not affected by an ambient environment before measuring the biological information.

9. The biological information measurement apparatus according to claim 1, wherein a correlation value calculation count, indicating a number of times the correlation value is calculated, is maintained, and
when the correlation value calculation count reaches a threshold without exceeding the correlation value threshold, electromagnetic waves corresponding with a highest correlation value obtained are applied to the living body in accordance with a change in a frequency of the ultrasound.

10. A biological information measurement method used in a biological information measurement apparatus, comprising:
applying ultrasound to a living body;
applying a first electromagnetic wave to a living body while the ultrasound is being applied to the living body;
receiving a first reflected wave corresponding to the first electromagnetic wave;
applying to the living body a second electromagnetic wave having a frequency different from a frequency of the first electromagnetic wave;
receiving a second reflected wave corresponding to the second electromagnetic wave;
calculating a correlation value between the first and second reflected waves;
determining whether the correlation value satisfies a given condition;
measuring biological information based on at least one of the first and second reflected waves when the determining determines that the correlation value satisfies a given condition;
counting correlation value calculations;
determining whether a calculation count is greater than a given calculation count threshold;
storing, in a correlation value storage unit, the calculated correlation value and the frequencies of the two electromagnetic waves corresponding to the calculated correlation value;
changing a frequency of ultrasound to be applied to the living body when the determining determines that the calculation count is greater than the calculation count threshold;
obtaining frequencies corresponding to a highest correlation value from the correlation value storage unit; and
applying two electromagnetic waves having the obtained frequencies to the living body when the determining determines that the calculation count is greater than the calculation count threshold,
wherein when determining whether the correlation value satisfies the given condition, a frequency applied to a subject is continuously changed by applying an output signal having a different frequency from a signal previously applied until the correlation value between the first and second reflected waves exceeds a correlation value threshold.

11. The biological information measurement method according to claim 10, wherein
the determining includes determining whether the correlation value is greater than the correlation value threshold, and
the measuring includes measuring the biological information when the determining determines that the correlation value is greater than the correlation value threshold.

12. The biological information measurement method according to claim 10, comprising:

applying to the living body a third electromagnetic wave having a frequency different from the frequencies of the first and second electromagnetic waves when the determining determines that the correlation value does not satisfy the given condition, receiving a third reflected wave corresponding to the third electromagnetic wave, calculating another correlation value between the second and third reflected waves, determining whether the other correlation value satisfies the given condition, and measuring the biological information based on at least one of the second and third reflected wave when the determining determines that the other correlation value satisfies the given condition.

13. The biological information measurement method according to claim 12, wherein
the applying includes applying the third electromagnetic wave to the living body when the determining determines that the correlation value is less than or equal to the correlation value threshold,
the determining includes whether the other correlation value is greater than the correlation value threshold, and
the measuring includes measuring the biological information when the determining determines that the other correlation value is greater than the correlation value threshold.

14. The biological information measurement method according to claim 10, wherein
the biological information measuring unit measures, as the biological information, an average value of the biological information measured based on each of the two reflected waves used to calculate the correlation value.

15. The biological information measurement method according to claim 10, wherein
the measuring includes measuring, as the biological information, a pulsation of the living body.

16. The biological information measurement method according to claim 10, wherein
the measuring includes measuring a blood pressure of the living body as the biological information.

17. The biological information measurement method according to claim 10, comprising:
determining that the first and second reflected waves are not affected by an ambient environment before measuring the biological information.

18. The biological information measurement method according to claim 10, wherein a correlation value calculation count, indicating a number of times the correlation value is calculated, is maintained, and
when the correlation value calculation count reaches a threshold without exceeding the correlation value threshold, electromagnetic waves corresponding with a highest correlation value obtained are applied to the living body in accordance with a change in a frequency of the ultrasound.

* * * * *